United States Patent [19]

Coquelet et al.

[11] Patent Number: 5,270,050

[45] Date of Patent: Dec. 14, 1993

[54] PARACETAMOL-BASED PHARMACEUTICAL COMPOSITION

[75] Inventors: Claude Coquelet, St. Gely du Fesc; Claude Bonne; Elisabeth Latour, both of Montpellier, all of France

[73] Assignee: Laboratoire Chauvin S.A., Montpellier, France

[21] Appl. No.: 773,574

[22] PCT Filed: Apr. 25, 1990

[86] PCT No.: PCT/FR90/00299

§ 371 Date: Nov. 12, 1991

§ 102(e) Date: Nov. 12, 1991

[87] PCT Pub. No.: WO90/13290

PCT Pub. Date: Nov. 15, 1990

[30] Foreign Application Priority Data

May 12, 1989 [FR] France .................................. 89 06295

[51] Int. Cl.⁵ .................... A61K 31/74; A61K 31/135
[52] U.S. Cl. ................................ 424/427; 514/912; 514/914; 424/45

[58] Field of Search ............................. 424/78.04, 427; 514/649, 912, 914; 560/19, 23; 562/453

[56] References Cited

U.S. PATENT DOCUMENTS 4,476,115 10/1984 Reed .................... 424/711
4,605,754 8/1986 Khanna .................. 562/553

OTHER PUBLICATIONS

W. F. Williams et al., "The utilization of carbon-13 and phosphorus-31 nuclear magnetic resonance spectroscopy in the study of the sorbitol pathway and aldose reductase inhibition in intact rabbit lenses", Exp. Eye Res. (1987) vol. 44, pp. 717-730.

Primary Examiner—Thurman K. Page
Assistant Examiner—Carlos Azpuru
Attorney, Agent, or Firm—Wenger, Cantor, Mueller & Player

[57] ABSTRACT

The object of the invention is an ophthalmic composition containing between 0.1 to 10% by weight of paracetamol in an ophthalmic excipient.

1 Claim, No Drawings

PARACETAMOL-BASED PHARMACEUTICAL COMPOSITION

The present invention relates to a paracetamol(n-acetyl-p-aminophenol)-based pharmaceutical composition.

Paracetamol is a compound well known for its antipyretic and analgesic activity.

This activity has been considered to be due to the inhibition of the synthesis of the prostallandins in the central nervous system. However, even though it inhibits the cyclo-oxygenase in the central nervous system, it shows no activity on this enzyme in the periphery (see, in particular, M. Scott Linscott, Clinical Therapeutics 9, 1, 1986).

Moreover, paracetamol has hitherto been administered, in practice, by the oral route.

The Applicant has made the surprising discovery that paracetamol administered to the eye has a useful pharmacological activity and may be used as an analgesic as well as for the treatment and prevention of cataracts.

Thus, the invention relates to an ophthalmic composition containing from 0.1 to 10% by weight of paracetamol in an ophthalmic excipient.

By ophthalmic excipient is meant an excipient which allows the administration of the active ingredient to the eye and which is not harmful to the eye. The composition may be made available in the form of an ophthalmic solution containing an aqueous solution, paracetamol and a buffer and, optionally, an antioxidant and a preservative.

The composition may also be constituted by an aqueous ophthalmic gel, an aqueous ophthalmic emulsion or an ophthalmic ointment.

Examples of ophthalmic compositions according to the invention will be given hereafter.

EXAMPLE 1

Collyrium Containing 1% Paracetamol

The following composition is prepared:

| | |
|---|---|
| Paracetamol | 1 g |
| Sodium metabisulfite | 0.1 g |
| EDTA | 50 mg |
| Benzalkonium chloride | 5 mg |
| $NaH_2PO_4$, $2H_2O$ | 0.38 g |
| $Na_2HPO_4$, $10H_2O$ | 1.6 g |
| NaCl | 0.16 g |
| Purified water qsp | 100 ml |

The composition has a pH between 6.8 and 7.2.

EXAMPLE 2

Ophthalmic Aerosol Containing Paracetamol

The composition of Example 1 may be packaged in an aerosol container.

EXAMPLE 3

Collyrium Containing 5% Paracetamol

The following composition is prepared:

| | |
|---|---|
| Paracetamol | 5 g |
| Sodium metabisulfite | 0.1 g |
| Nipagine | 26 mg |
| Nipasol | 14 mg |
| $NaH_2PO_4$, $2H_2O$ | 0.38 g |
| $Na_2HPO_4$, $10H_2O$ | 1.6 g |
| Cremophore$^R$ | 25 g |
| Water qsp | 100 ml |

EXAMPLE 4

Paracetamol-Based Ophthalmic Gel

1% carbopol is added to the composition of Example 1. The pH is adjusted to 7 with NaOH.

EXAMPLE 5

Paracetamol-Based Ophthalmic Ointment

The following composition is prepared:

| | |
|---|---|
| Paracetamol | 5 g |
| Vaseline | 50 g |
| Viscous vaseline oil | 15 g |
| Lanolin | 35 g |

EXAMPLE 6

Ophthalmic Emulsion

The following emulsion is prepared:

| | |
|---|---|
| Paracetamol | 1 g |
| Sodium metabisulfite | 0.1 g |
| EDTA | 50 mg |
| Benzalkonium chloride | 5 mg |
| $NaH_2PO_4$, $2H_2O$ | 0.38 g |
| $Na_2HPO_4$, $10H_2O$ | 1.6 g |
| NaCl | 0.16 g |
| Cremophore$^R$ | 10 g |
| Fatty excipient | 30 g |
| Water qsp | 100 ml |

Pharmacological results demonstrating the properties of the compositions according to the invention are given below.

I. Effect on Photokeratitis Induced by UV-B in the Rabbit

10 Male, albino New Zealand rabbits of means weight 2 kg and free of any ocular infection (prior ophthalmic examination) are used for the assays.

The irradiations were performed as follows:

50 µl of physiological serum were instilled into the left eye. The animals were placed in a restraining cage under UV light. The left eye was irradiated with UV-B (312 nm) (the right eye being protected) at an intensity of 0.4 J/day (which corresponds to 3'30" of exposure) for 7 days.

Macroscopic ocular examinations were made every day.

Criteria of evaluation applied:
 redness and edema of the nictitating membrane and the palpebral and bulbar conjunctivae,
 corneal opacity
 neovascularization of the cornea.

Scoring scale used:
 (1) Nictitating membrane and palebral and bulbar conjunctivae
 very slight redness and edema 1
 slight redness and edema 2
 moderate redness and edema 3
 quite considerable redness and edema 4 marked redness and edema 5
very marked redness and edema 6
(2) Degree of corneal opacity
presence of a diffuse translucent zone
presence of a readily identifiable translucent zone; iris clearly visible
presence of a slightly opalescent zone; iris discernible
presence of an opalescent zone; iris invisible.
(3) Neovascularization
presence of a few small vessels
presence of quite a number of small vessels
presence of many small vessels or a few large vessels
presence of very many small vessels or many large vessels
presence of very many large vessels.

Treatment

These animals were divided into 2 homogeneous groups of 5 animals (groups A and B) on the basis of the scores obtained after the last period of irradiation.

The treatment was started after the last period of irradiation: instillations of 25 µl of the collyrium under test (see Table I) in the left eye 4 times a day at intervals of 2 h S 30.

TABLE I

|  | Collyrium B | Collyrium A |
| --- | --- | --- |
| Paracetamol | 1.000 g | — |
| Benzalkonium chloride | 0.005 g | 0.005 g |
| Sodium metabisulfite | 0.100 g | 0.100 g |
| Monosodium phosphate 2H₂O | 0.380 g | 0.380 g |
| Disodium phosphate 12H₂O | 1.600 g | 1.600 g |
| Sodium chloride | 0.160 g | 0.386 g |
| Purified water qsp | 100.000 ml | 100.000 ml |
| pH | 6.81 | 6.77 |

Results

The results are presented in Table II and demonstrate an improvement of opacity and corneal neovascularization in the rabbits treated with the eye lotion B according to the invention, as from the 5th day of treatment.

TABLE II

Sums of the scores determined after observations of the rabbits in groups A and B

| | nictitating membrane | bulbar conjunctiva | palpebral conjunctiva | opacity | neovascularization |
| --- | --- | --- | --- | --- | --- |
| 1st day | | | | | |
| Group A | 28 | 25 | 28 | 13 | 13 |
| Group B | 30 | 28 | 39 | 14 | 13 |
| 3rd day | | | | | |
| Group A | 16 | 14 | 15 | 9 | 18 |
| Group B | 19 | 12 | 17 | 7 | 15 |
| 5th day | | | | | |
| Group A | 14 | 7 | 9 | 6 | 12 |
| Group B | 14 | 7 | 10 | 4 | 11 |
| 7th day | | | | | |
| Group A | 10 | 6 | 8 | 6 | 9 |
| Group B | 9 | 3 | 6 | 1 | 5 |
| 9th day | | | | | |
| Group A | 7 | 3 | 5 | 3 | 6 |
| Group B | 6 | 2 | 5 | 0 | 1 |

II- Effects on the Rupture of the Blood-Aqueous Barrier Induced by Paracentesis in the Rabbit Paracentesis of the anterior chamber in the rabbit causes ocular inflammation characterized by various signs: hyperemia, myosis, increase in intraocular pressure and rupture of the blood-aqueous barrier.

This ocular traumatism also involves release of prostaglandins, in particular PGE2, into the aqueous humor. These endogenous prostaglandins play an important role in the rupture of the blood-aqueous barrier.

The experiments were performed on female New Zealand rabbits, of mean weight 2 kg and locally anesthetized by instillation of Cebesine[R].

The primary aqueous humor (about 0.1 ml) was withdrawn from both eyes by puncture through the cornea into the anterior chamber while avoiding any contact of the needle with the anterior face of the iris and the crystalline lens.

A second paracentesis was performed SO minutes later after the animal had been sacrificed by means of pentobarbital sodium (120 mg/kg i.v.): the secondary aqueous humor thus obtained was diluted ¼ with heparin in order to prevent coagulation due to fibrin.

The protein concentration in the aqueous humor was measured according to the method of Lowry et al. (J. Biol. Chem. 193, 265-275, 1951).

The animals were treated by instillation of 25 µl of the test solution into both eyes 20 and 10 mn before paracentesis.

The group of animals treated with a reference solution was included.

The formulae of the ophthalmic solutions are the following:

TABLE III

| | Composition | |
| --- | --- | --- |
| | reference solution | 3% paracetamol solution |
| Paracetamol | — | 0.300 g |
| PEG 400 | 5.000 g | 5.000 g |
| Water qsp | 10.000 ml | 10.000 ML |

The pretreatment by means of paracetamol in a 3% ophthalmic solution significantly inhibits protein extravasation and the increase in the level of PGE2 in the aqueous humor (Tables IV and V).

Paracetamol is classically described as a very weak inhibitor of PG synthetase, with the exception of that contained in cerebral tissue (Bowman W. C. and Rand J. J. "textbook of pharmacology", 2nd ed. Oxford, Blackwell, 1980).

In this ocular traumatic model, paracetamol does, however, inhibit the release of PGE2 into the aqueous humor by an unknown mechanism, and hence the rupture of the blood-aqueous barrier.

TABLE IV

Inhibition of the extravasation of protein induced by paracentesis after instillation of paracetamol

| Treatment | Proteins (mg/ml) | Inhibition (%) | (n) |
| --- | --- | --- | --- |
| Reference solution | 34.3 +/− 9.3 | — | (10) |
| 3% Paracetamol | 23.2 +/− 11.2 | 32 | (9) | n: number of measurements per group

TABLE V

Inhibition of the increase in the level of PGE2 in the aqueous humor induced by paracentesis

| Treatment | PGE2 (mg/ml) | Inhibition (%) | (n) |
| --- | --- | --- | --- |
| Reference solution | 4.8 +/− 1.3 | — | (9) |

TABLE V-continued

Inhibition of the increase in the level of PGE2 in the aqueous humor induced by paracentesis

| Treatment | PGE2 (mg/ml) | Inhibition (%) | (n) |
| --- | --- | --- | --- |
| 3% Paracetamol | 3.0 +/− 0.6 | 34 | (7) | n: number of measurements per group

We claim:
1. Method for the treatment of ocular pain or inflammation comprising topically administering a composition comprising 0.1–10% by weight of N-acetyl-p-aminophenol to the eye.

* * * * *